(12) United States Patent
Straaijer

(10) Patent No.: US 8,681,312 B2
(45) Date of Patent: Mar. 25, 2014

(54) INSPECTION APPARATUS FOR LITHOGRAPHY

(75) Inventor: Alexander Straaijer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 649 days.

(21) Appl. No.: 12/920,968

(22) PCT Filed: Mar. 20, 2009

(86) PCT No.: PCT/EP2009/002077
§ 371 (c)(1),
(2), (4) Date: Oct. 20, 2010

(87) PCT Pub. No.: WO2009/115342
PCT Pub. Date: Sep. 24, 2009

(65) Prior Publication Data
US 2011/0032500 A1  Feb. 10, 2011

Related U.S. Application Data

(60) Provisional application No. 61/064,686, filed on Mar. 20, 2008.

(51) Int. Cl.
*G03B 27/42* (2006.01)

(52) U.S. Cl.
USPC ............ 355/53; 355/55; 355/63; 355/67; 355/77; 356/351

(58) Field of Classification Search
USPC ............ 355/53, 55, 63, 67, 77; 356/351, 354, 356/359, 498
See application file for complete search history.

(56) References Cited

U.S. PATENT DOCUMENTS

| 5,757,494 | A | 5/1998 | Green et al. |
| 5,880,838 | A | 3/1999 | Marx et al. |
| 6,515,745 | B2* | 2/2003 | Vurens et al. ............... 356/369 |
| 2006/0066855 | A1* | 3/2006 | Boef et al. .................. 356/401 |
| 2006/0221331 | A1* | 10/2006 | Elyasaf et al. ............ 356/237.1 |
| 2008/0198380 | A1* | 8/2008 | Straaijer et al. ............ 356/369 |

FOREIGN PATENT DOCUMENTS

EP  1 628 164 A2  2/2006

OTHER PUBLICATIONS

International Search Report mailed Jun. 22, 2009 for International Application No. PCT/EP2009/002077, 4 pgs.
Written Opinion mailed Sep. 21, 2010 for International Application No. PCT/EP2009/002077, 4 pgs.

* cited by examiner

*Primary Examiner* — Steven H Whitesell Gordon
*Assistant Examiner* — Mesfin T Asfaw
(74) *Attorney, Agent, or Firm* — Sterne, Kessler, Goldstein & Fox P.L.L.C.

(57) ABSTRACT

The measurement of two separately polarized beams (Ix, Iy) upon diffraction from a substrate (W) in order to determine properties of the substrate is disclosed. Circularly or elliptically polarized radiation is passed via a variable phase retarder in order to change the phase of one of two orthogonally polarized radiation beams with respect to the other of the two beams. The phase change is dependent on the wavelength of the polarized beam. The relative phases of the two radiation beams and other features of the beams as measured in a detector gives rise to properties of the substrate surface.

20 Claims, 6 Drawing Sheets

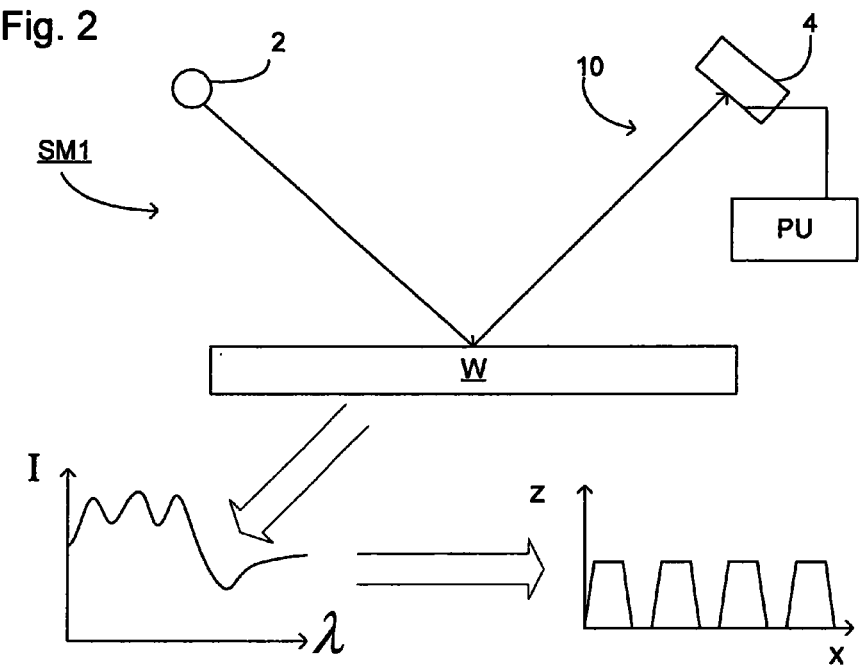
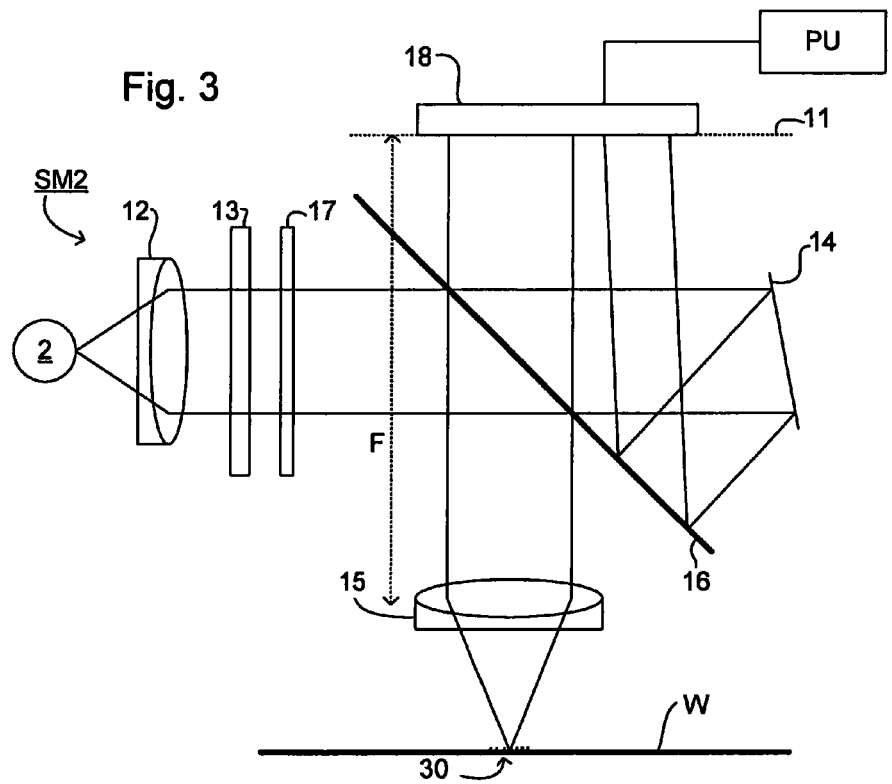

INSPECTION APPARATUS FOR LITHOGRAPHY

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

SUMMARY

Although scatterometry is a relatively quick form of analysis of a surface, measuring only the intensity of scattered radiation may not be the most precise of measurements, as it does not take into account the different behavior of radiation that is polarized in different directions. For example, if the substrate object that is being measured is in the form of a grating that is aligned with one polarization direction, radiation polarized in that direction will scatter in a very different manner from radiation polarized in the orthogonal direction. To take polarization directions into account, an ellipsometric system has been envisaged that enables certain parameters of orthogonally polarized beams to be measured.

However, all of the solutions conceived incorporate several different devices, each of which has to be calibrated and which will absorb a certain amount of the radiation beam each time the beam passes through it. Furthermore, having several devices in series risks exacerbating a small error in even only a single one of those devices. Yet furthermore, not all azimuthal angles are useable. Potentially useful information is therefore lost.

It is desirable, for example, to provide an ellipsometric function in a scatterometer such that phase difference and amplitude of a beam diffracted from a structure may be measured throughout the entire azimuthal range.

According to an aspect of the present invention, there is provided an inspection apparatus, a lithographic apparatus and a lithocell configured to measure a property of a substrate, the inspection apparatus including an optical element configured to focus a radiation beam onto a substrate at a range of incident and azimuth angles such that the radiation beam reflects from the substrate; a polarizing device configured to polarize the radiation beam into two different polarization directions; a variable retarder configured to retard the two polarization directions by a certain amount so as to impose a variable phase shift on the reflected radiation beam, the variable phase shift being dependent on the wavelength of the radiation beam; and a detector system configured to detect simultaneously an angle-resolved spectrum of the two polarization directions of the radiation beam.

According to another aspect of the invention, there is provided a method of measuring a property of a substrate, the method including providing a radiation beam with elliptical polarization; reflecting the radiation beam off the surface of a substrate; splitting the reflected radiation beam into two polarized sub-beams; shifting the phase of a first sub-beam by a variable amount with respect to a second sub-beam, the variable amount being dependent on the wavelength of the radiation beam; and simultaneously detecting the sub-beams.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 2 depicts a first scatterometer in accordance with an embodiment of the invention;

FIG. 3 depicts a second scatterometer in accordance with an embodiment of the invention;

DETAILED DESCRIPTION

Figure 1A:
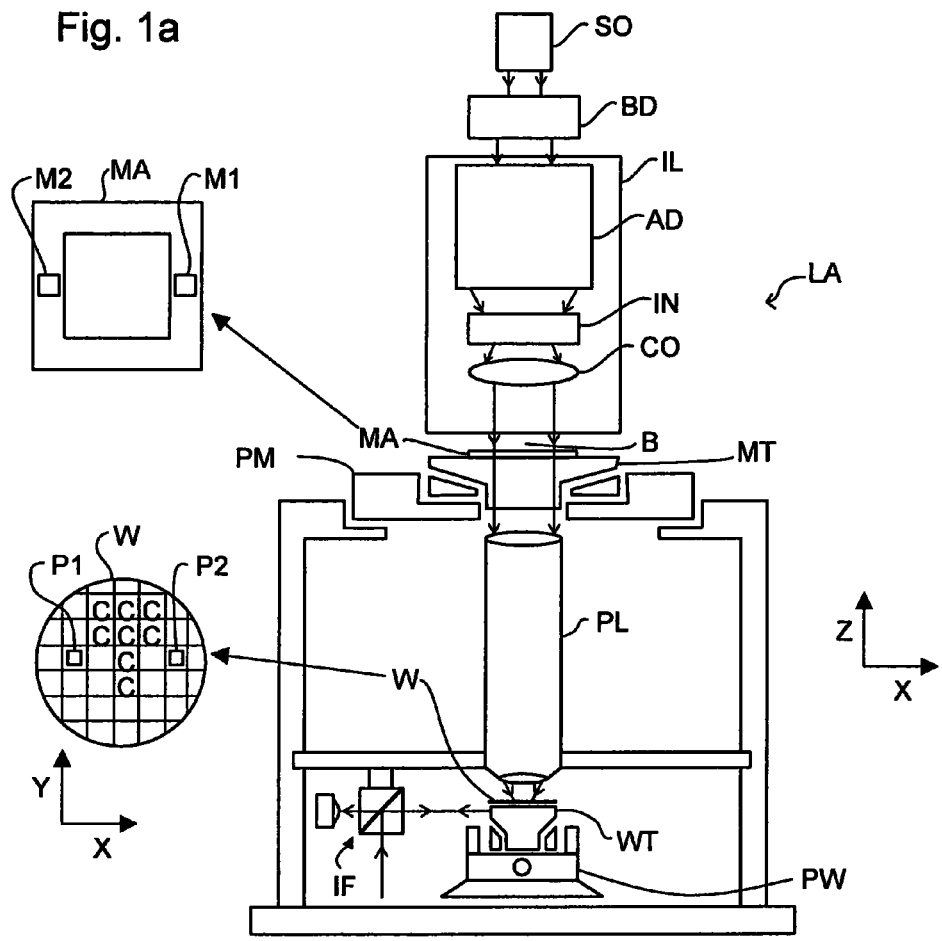
FIG. 1a depicts a lithographic apparatus in accordance with an embodiment of the invention.

FIG. 1*a* schematically depicts a lithographic apparatus. The apparatus includes an illumination system (illuminator) IL configured to condition a radiation beam B (e.g. UV radiation or EUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1*a*, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1*a*) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
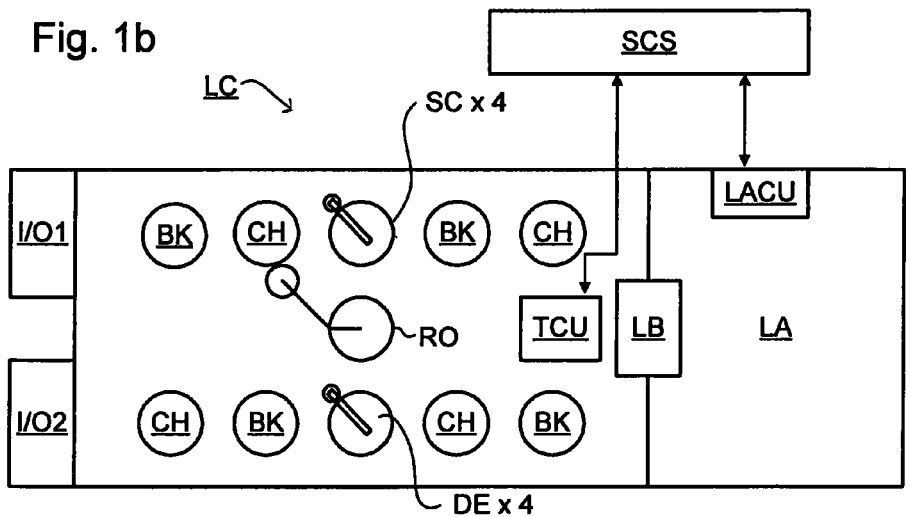
FIG. 1b depicts a lithographic cell or cluster in accordance with an embodiment of the invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB), which is customarily the first step carried out on exposed substrates and which increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 2 depicts a scatterometer SM1 which may be used in embodiments of the present invention. It includes a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used with an embodiment of the present invention is shown in FIG. 3. In this device, the radiation emitted by radiation source 2 is focused using lens system 12 through interference filter 13 and polarizer 17, reflected by partially reflected surface 16 and is focused onto a target 30 of the substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beamsplitter 16 part of it is transmitted through the beamsplitter as a reference beam towards a reference mirror 14. The reference beam is then projected onto a different part of the same detector 18.

A set of interference filters 13 is available to select a wavelength of interest in the range of, say, about 405-790 nm or even lower, such as about 200-300 nm. The interference filter may be tunable rather than including a set of different filters. A grating could be used instead of interference filters.

The detector 18 may measure the intensity of scattered radiation or light at a single wavelength (or narrow wavelength range), the intensity separately at multiple wavelengths or integrated over a wavelength range. Furthermore, the detector may separately measure the intensity of transverse magnetic- and transverse electric-polarized radiation or light and/or the phase difference between the transverse magnetic- and transverse electric-polarized radiation or light.

Using a broadband radiation source (i.e. one with a wide range of radiation frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least 2 $\delta\lambda$ (i.e. twice the wavelength). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in European Patent Application Publication No. EP 1,628,164A, which is incorporated herein by reference.

The target on substrate W may be a grating, which is printed (for example, using the lithographic system described above) such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings (and thus determine whether there are errors in any part of the lithocell or in the alignment of the substrate with respect to the lithocell that manifest themselves as variations in the target). The parameters of the grating, such as line widths and shapes, may be input to the reconstruction process, performed by processing unit PU, from knowledge of the printing step and/or other scatterometry processes.

Figures 4, 5:
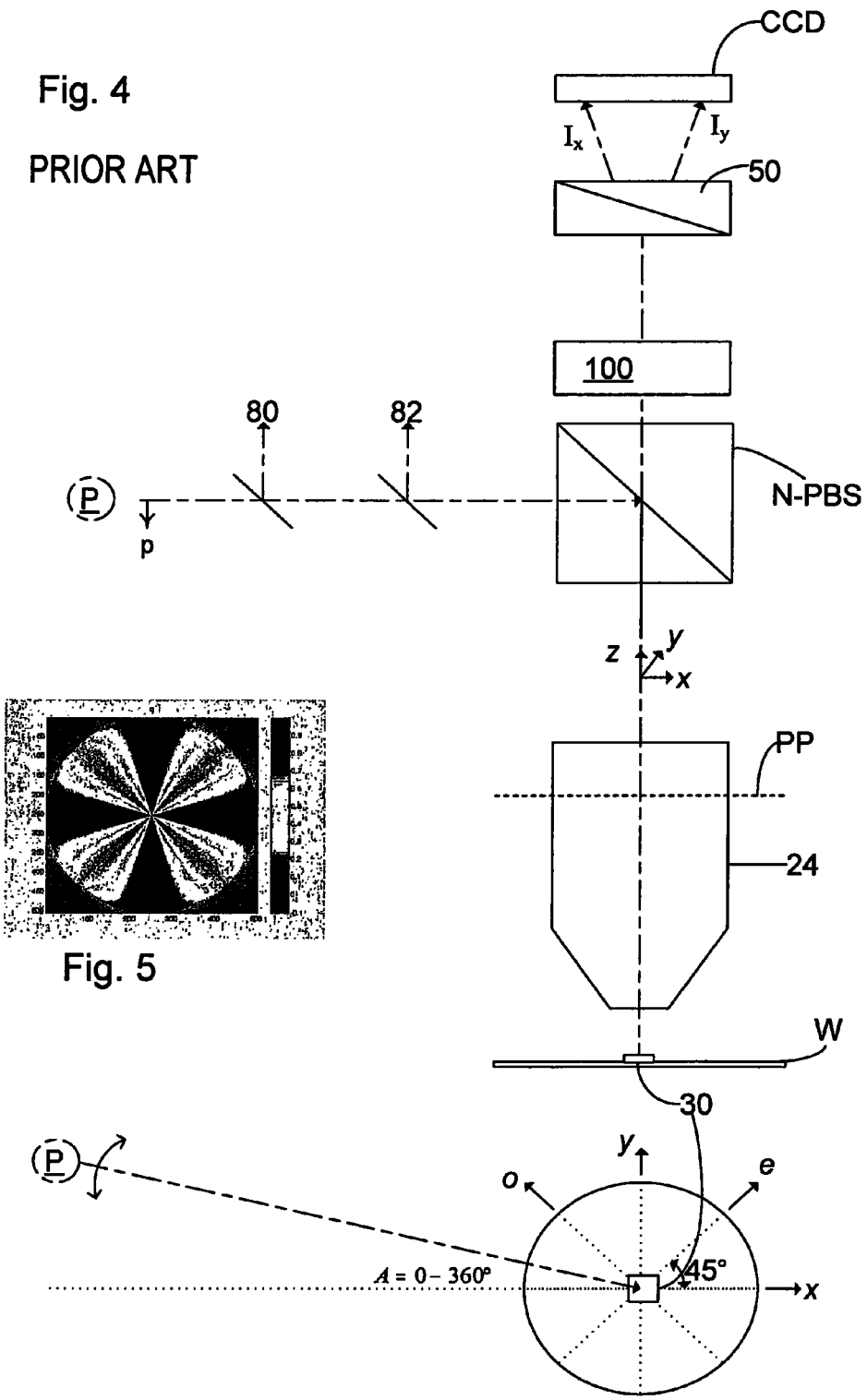
FIG. 4 depicts an inspection apparatus.
FIG. 5 depicts a radiation image according to the inspection apparatus of FIG. 4.

As discussed above, a development from a simple scatterometer is an ellipsometer, which may be used to determine the shapes and other properties of structures on a substrate using slightly different parameters of the reflected radiation. The way this is done is that an incident beam is reflected from a substrate W as shown in FIG. 4, this incident beam reflecting off the target structure 30. The reflected beam passes through a microscope objective 24, through a non-polarizing beamsplitter N-PBS and through focusing lenses (or other optics) onto a camera CCD.

FIG. 4 shows an example of a known ellipsometric sensor (or an ellipsometer) that seeks to measure not only the behavior of differently-polarized radiation, but also the phase difference between differently-polarized radiation beams. In the system shown in FIG. 4, illumination radiation from source P is reflected from a structure 30 on a target portion of a substrate W and on its return journey from the substrate, it is linearly polarized along one of the two eigen-polarizations of three beamsplitters that are present in the sensor (the eigen-polarizations being measured with respect to the x or y direction as shown in FIG. 4). A first beamsplitter N-PBS reflects part of the illumination to two further beamsplitters: one beamsplitter 80 sends part of the illumination to an imaging branch; and another beamsplitter 82 sends part of the illumination to a focus branch. The first beamsplitter N-PBS is a non-polarizing beamsplitter that directs the rest of the beam to a camera CCD. Having passed through the non-polarizing beamsplitter N-PBS, the polarized beam passes through a fixed-phase shifter 100 whose ordinary and extraordinary axes have been positioned at 45° with respect to the x and y directions as illustrated on the bottom of FIG. 4. Subsequently, the beam is divided into its respective x- and y-polarization orientations using a Wollaston prism 50 and impinges on a camera (or sensor or detector) CCD. The relative intensities of the polarized beams are used to determine the relative polarization orientations of the different parts of the beam. From the relative polarization orientations, the effect of the structure 30 on the beam as a whole can be determined because different reflecting edges of structures will affect the differently polarized states of radiation in different ways.

From the effect the structure 30 has on the beam, the properties of the structure itself can be determined. The beam is reflected off the structure from several incident angles and from some azimuthal angles. The resulting intensity image is shown in FIG. 5. Smaller angles of incidence give rise to intensities toward the middle of the intensity image, such that a beam incident along the normal and reflecting along the normal gives rise to the intensity measurement in the middle of the image of FIG. 5. The intensity variation in a circumferential direction is linked to the azimuthal angle of the radiation beam. If an incident beam is polarized such that it is s-polarized in one direction and p-polarized in the orthogonal direction, the two polarization directions will react differently to being reflected from a surface. Even if the surface is flat, if the azimuthal angle is such that the reflecting surface is aligned with one of the polarization directions, that polarization direction will survive intact, while the orthogonal polarization direction will be annihilated. In this way, there are two orthogonal directions (or azimuthal angles) from which only one polarization state will survive and only the information from that polarization state will be available for manipulation to determine the properties of the surface or structure from which the beam was reflected. At 45° to these orthogonal directions, equal amounts of the two orthogonally polarized portions of radiation beam will survive to the detector and form part of the image. When using the fixed-phase shifter 100, the phase shift applied to the radiation beam needs to be estimated and this is done using the first line of equation (9) below. The polarized beam undergoes a phase shift and the intensities of the two polarized directions are then detected by the detector CCD. Knowing these intensities and knowing the original azimuthal angle of the incident beam, an iterative process can be carried out to estimate the phase shift that was applied. The applied phase shift is not accurately known because it varies depending on the wavelength of the incoming beam and is often applied using only a quarter-waveplate, which may not be very accurate. Because the phase shift needs to be estimated, a detector result with the intensities of both s- and p-polarization directions is desired. This means that only the detector results on the diagonals (i.e. for azimuthal angles of 45° and 135°) can be used for the derivation of the resultant phase difference A as described below. It is therefore only these diagonal measurements that provide useful information on how the reflected beam was affected by the structure. The bright areas showing high intensity on FIG. 5 illustrate this.

U.S. Pat. No. 5,880,838 (Marx et al.) also describes the measurement of a structure on a substrate using ellipsometry, wherein the measurement system is called polarization quadrature measurement (PQM). This document describes focusing a polarized beam of radiation (with TE and TM fields) onto the structure. The TM and TE fields are affected differently by the diffraction off the structure. The TE field can be used as a reference to analyze the phase and amplitude changes in the TM field. The relationship between phases and amplitudes of the TE and TM fields is dependent on the structural parameters (e.g. the depth of a hole or the height of a grating bar or the pitch of a grating) of the structure. By measuring this relationship, therefore, the structural parameters may be determined.

Further to measuring the intensity variation within an illumination beam, ellipsometry is the measurement of the state of polarization of scattered radiation. Ellipsometry measures two parameters: the phase difference ($\Delta$) between two differently polarized beams and an amplitude ratio (tan $\Psi$) of two polarized beams. With these two parameters, any polarization state of a purely polarized beam may be described.

Specifically, if an incident beam has both s and p polarizations, the reflected beam will have reflectance coefficients $R_p$ and $R_s$. $\Delta$ (Delta) is the phase difference between the reflectance coefficients $R_p$ and $R_s$ as given in equation (1) below.

The intensity of the received beam is proportional to the sum of the amplitudes, taking into account the angle of their relative polarization. For example, if the polarizations of both $R_p$ and $R_s$ are aligned in the same orientation, the intensity of the received beam is at a maximum. If the two amplitudes are in orthogonal orientations, they cancel each other out and the intensity is at a minimum. The ratio between the amplitudes of the two polarization directions (or orientations) is tan $\Psi$ and so the relationship between $\Psi$ and $R_p$ and $R_s$ is as follows in equation (2).

$$\Delta = arg(R_p - R_s) \quad (1)$$

$$\tan \Psi = R_p / R_s \quad (2)$$

Ellipsometry compares the reflectance of the p-polarized component with the s-polarized component. When using linearly polarized radiation, on azimuth angles (A) of 0 and 90°, information from the other polarization angles will be missing so that ellipsometry using the fixed-phase shifters is found to contain useful information only at azimuth angles of A=45° and 135°, which are at an angle to the polarized components and do not cancel out those components.

Further ideas of comparing differently-polarized beams have been proposed in the past. Some in particular have, as their aim, the obtaining of four differently polarized reflected sub-beams from a single incident beam in order to measure, from a measured intensity of each sub-beam, the difference in amplitude and phase of the four known polarizations. A first potential solution does this by having the reflected beam pass through two polarizing beamsplitters arranged at 90° with respect to each other such that a radiation beam is split into two orthogonally polarized sub-beams and each of those polarized sub-beams is subsequently split at a 90° angle into mutually orthogonally polarized sub-sub-beams. All four sub-beams are therefore at 0, 90, 180 and 270° polarization angles (with respect to each other). Wollaston prisms and the like are also used to split the beam into sub-beams, and each beam polarized by a different angle. An alternative solution that has been proposed is to have the beam pass through a single polarizing device that has four quadrants, each quadrant with a polarizer having a different polarizing angle such that the one beam is effectively divided into four quadrants, each polarized in a different direction (for example, 0, 45, 135 and 180°). In any of the solutions above, separate sub-beams of different polarizations are compared on the same or different cameras and the effect of the object on the substrate compared for the different polarization angles. Analysis of the image on the camera gives rise to the characteristics of the structure from which the radiation beam has been reflected.

In the previously envisaged embodiment discussed above, the beam is split by a further beamsplitter 50 and directed onto the camera CCD. At this point, the beam is either a TM (transverse magnetic) polarized beam or a TE (transverse electric) polarized beam. The pupil plane PP of the microscope objective 24 is shown in FIG. 4. It is at this pupil plane PP that the microscope objective focuses the radiation that is reflected and scattered from the surface of the substrate W. The image that is created at this pupil plane PP is subsequently recreated on the camera CCD using lenses or other optics such that the acquired image contains the largest amount of information possible (i.e. because there is no loss of sharpness or scattering of radiation outside of the aperture of the camera CCD).

FIG. 4 also shows a fixed-phase shifter 100 positioned between the non-polarizing beamsplitter N-PBS and the beamsplitter 50 that separates the polarized beams prior to transmitting those polarized beams to the camera CCD. An eo-coordinate system that is orientated along the extraordinary and ordinary axes of the fixed-phase shifter 100 is also shown in FIG. 4 as a circle and shows a relative position of the extraordinary and the ordinary axes compared to the y and x axes of the system. $E_o$ and $E_e$ are the unknown complex amplitudes of the scattered fields along, respectively, the e and o directions. For the purposes of embodiments of the present invention, only the real parts of the complex amplitudes dealing with reflectance R (hence $R_o$ and $R_e$ or $R_s$ and $R_p$) are dealt with. In this system, it is this reflectance, compared with the changed phase as predefined by the phase modulator, which enables the system to determine the parameters of the structure 30.

Embodiments of the present invention provide benefits over the fixed-phase shifter (or modulator). In an embodiment of the present invention, instead of using a fixed-phase shifter 100, the phase shift (or retardation δ) is varied using a variable retarder 110. The variable retarder 110 introduces a deliberate phase-shift between two components of the polarized beam.

Figure 6:
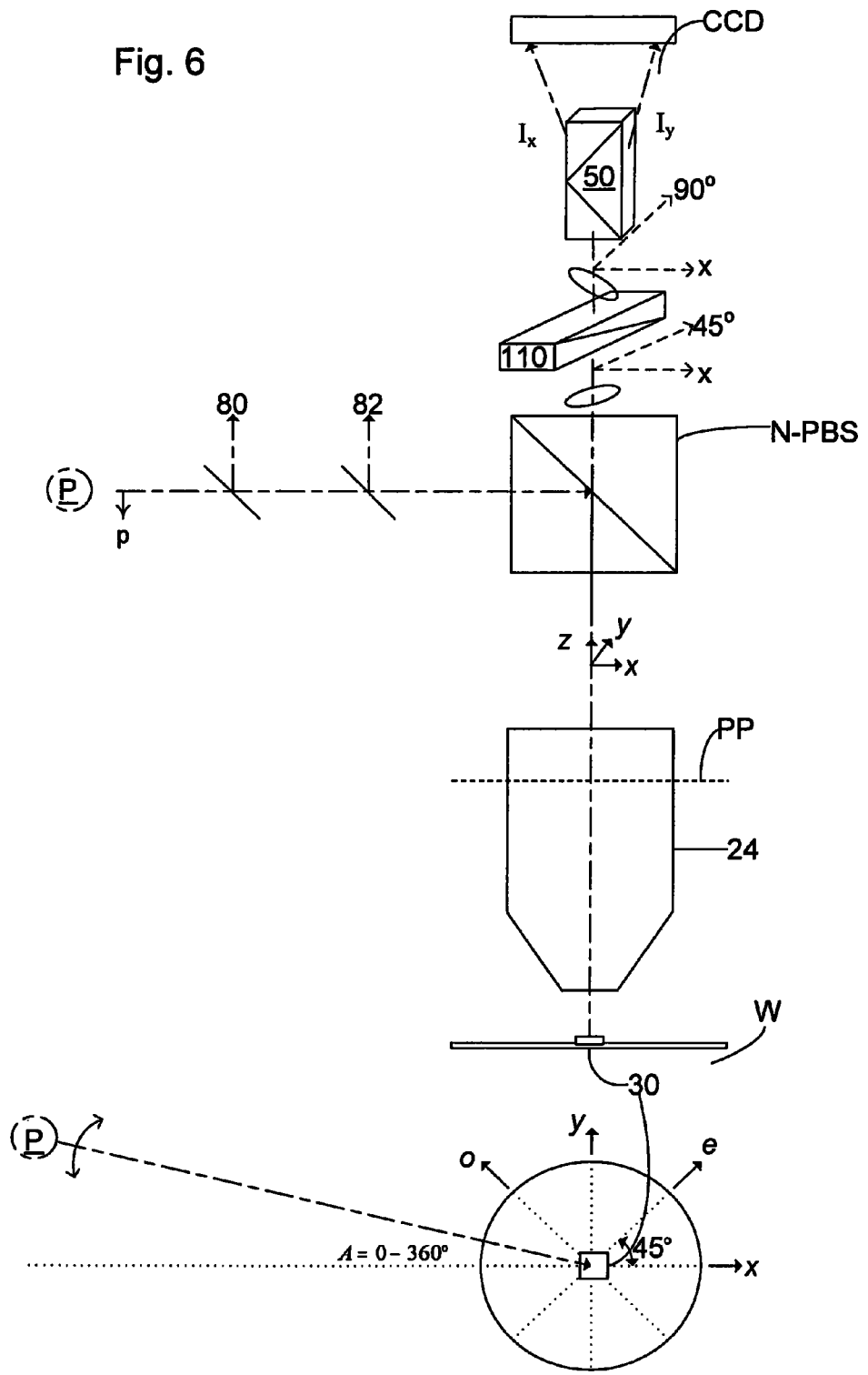
FIG. 6 depicts an inspection apparatus according to an embodiment of the present invention.

The variable retarder 110 needs to be positioned at an angle to both the x-axis) (0°) and y-axis (90°) in order to have an effect on both polarization directions. If the variable retarder were parallel to either axis, it would not have any effect on the beam intensities. The variable retarder 110 is therefore aligned at 45° with respect to the x-axis of the beam as shown in FIG. 6, i.e. half-way between the x- and y-axes. The phase-shift or retardation provided by the variable retarder 110 changes with variations in the wavelength of the reflected radiation beam. Clearly, a wavelength in a radiation beam will need a different amount of retarding of at least one polarization direction to create the same phase shift as for another wavelength. This is because the relative position of the peaks and troughs of the various linear waves that are superimposed to create a complex polarized beam is what gives rise to the overall polarization state. For example, s- and p-polarized linear waves with their peaks at the same timing or same position in the direction of the wave will give rise to a linearly polarized beam. S- and p-polarized waves phase-shifted by 90° give rise to circularly polarized radiation. Elliptically polarized radiation is caused by any other phase shift. Any phase difference between the linear waves will cause destructive (and constructive) superposition of the differently-oriented intensities, resulting in, for example, an elliptically polarized radiation beam.

The variable retarder according to an embodiment of the present invention therefore adjusts its retardation depending on the incoming wavelength to obtain the desired phase shift, δ.

An apparatus according to an embodiment of the present invention is depicted in FIG. 6. Radiation of a fixed wavelength from a source P with a known polarization state p is reflected from the target 30 on the surface of the substrate W to be investigated. For calibration purposes, the target 30 may be simply the plane surface of the substrate. The radiation may be linearly polarized, or it may have another form of polarization such as circular polarization or radial polarization, etc. In the case of circular polarization, the polarizing device that polarizes the radiation is combined with a retarder to retard one direction of radiation, thus creating circularly polarized radiation. Any measurable polarization may be used.

The radiation reflects at multiple angles of incidence (for example $θ_i$=0-80°) and at all azimuth angles (A=0-360°). It will be appreciated that ranges within these ranges (or even outside of the listed range for the angle of incidence) may also be selected for calibration and other purposes, depending on the processing capacity available. The range of azimuthal angles may be applied using various numbers of steps. The entire range may be covered in 36 steps of 10°, or even in just 3 steps of 120°, or each degree may be measured individually. The larger the number of steps, the smaller the number of degrees per step and the more information is available for the determining of the parameters of the structure on the substrate being measured. However, this is balanced with the throughput time. More calculations obviously take more time and/or more computing power.

The reflected radiation beam (as the incident radiation beam) consists of a full available range of radiation rays with different polarization states. The reflected radiation is received by a microscope objective 24 and focused on the pupil plane PP, which is reproduced at camera CCD for the same reasons as given with respect to FIG. 4 above.

Figure 9:
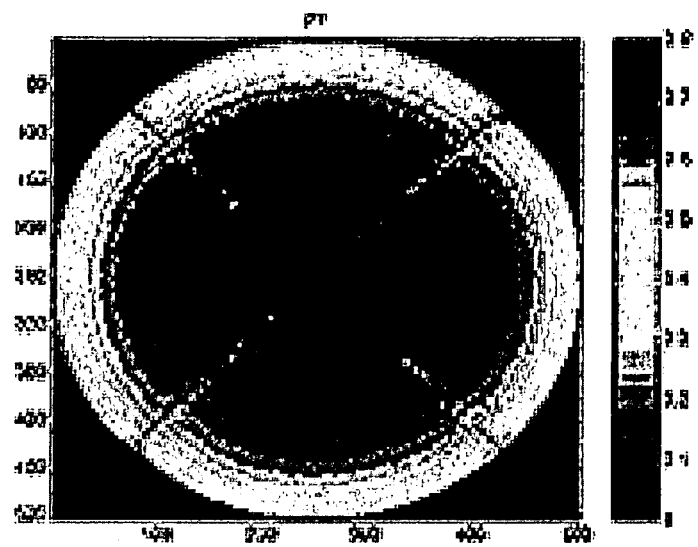
FIGS. 9 and 10 depict the measurement of ellipsometric data according to an embodiment of the present invention.

The radial position of the measured radiation beam is proportional to the angle of incidence of the incident beam. Its azimuth angle A is calculated from the positive x-axis as shown on the bottom of FIG. 7, where the azimuth angle of the incident beam is labeled as Ai. During the calibration step, the radiation beam is detected and recorded at all angles of incidence and all azimuth angles and is reflected from a plane surface such that the polarization states of the beam should all be measurable at some point. Knowing what a radiation beam will "look" like depending on its angle of incidence and its azimuth angle enables a description of the radiation beam in polar coordinates, which is useful for measurements at the CCD camera of the reflected radiation beam. The "description" of the radiation beam may take the form of an image as shown in FIG. 9, where the centre of the image shows the intensity of radiation that is reflected along the normal N (or z-axis z of FIG. 7) to the substrate, and the outer periphery of the image shows the intensity of the radiation that is reflected at a maximum angle from the normal N (e.g. 80°).

A basic set up of a scatterometer such as that shown in FIG. 2 or FIG. 3 is used. A microscope objective 24 receives a beam that is reflected from the structure 30 present on the substrate W. The incident beam may have passed through the microscope objective before reflecting off the structure 30, or it may have been focused using other means. In order to be able to measure a reflected beam for all azimuth as well as incident angles, the incident beam has circular (and more beneficially elliptical) polarization rather than linear polarization, enabling all directions of polarization to be measured and reducing the risk of loss of some of the beam during reflection. The risk of loss is reduced because even if information from one polarization state is lost, several polarization states remain to be measured at any given combination of incidence and azimuthal angle.

The incident radiation for each measurement is of a fixed wavelength and has a known polarization state. The same wavelength and polarization state is investigated at multiple angles of incidence (0-80°) and at all azimuth angles (0-360°) as described above. The returning or reflected radiation beam consists of an effectively infinite number of rays with different polarization states.

FIG. 6 shows a combined radiation beam that is elliptically polarized and enters a non-polarizing beamsplitter N-PBS where about 50% of the radiation will be transmitted and 50% will be reflected (though beamsplitters can be manufactured and used herein to transmit and reflect various percentages of incident radiation). The ellipsometric data of the transmitted beam are measured by separating the energy of the x- and y-polarized components $I_x$ and $I_y$ of the transmitted beam with the help of a polarizing beamsplitter 50 (for instance a Wollaston prism). This gives rise to the orthogonally polarized sub-beams. The relative phase of the sub-beams with different polarization states needs to be changed in order to be compared to give a full picture of the state of the beam reflected from the structure (for example, to measure by how much the relative phase difference changes or so that the recombined sub-beams create circularly or elliptically polarized radiation, which gives rise to the useful images created by the camera).

Figure 7:
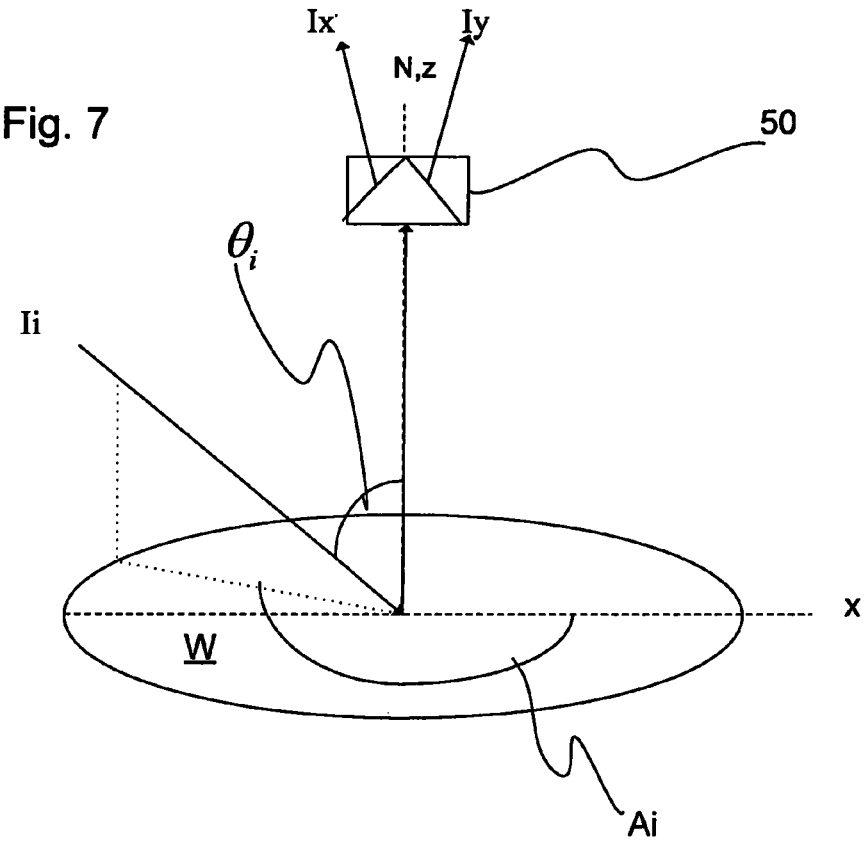
FIG. 7 depicts the behavior of a radiation beam according to an embodiment of the present invention.
Figure 8:
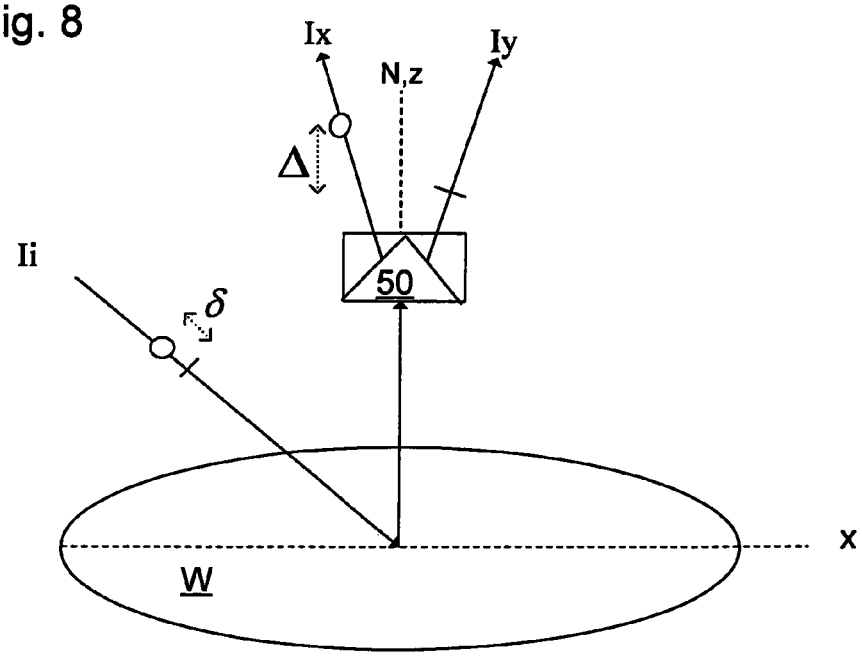
FIG. 8 depicts the behavior of polarization states of a radiation beam in accordance with an embodiment of the invention.

The phase-shift or retardation δ between the e and o amplitudes can be varied by the variable retarder. FIG. 8 shows a first polarization direction as a circle and a second polarization direction as a line across the beam direction. The retardation δ is shown as the distance between these two representative symbols. The retardation δ is may be in the region of 90 or 270°, for instance. FIG. 7 shows an incident beam with an intensity $I_i$, at an incident angle $\theta_i$ from the normal N or z-axis z and an azimuth angle $A_i$ from the x-axis. The incident beam reflects from the surface of the substrate W and is sent in a new direction as a reflected beam toward the detector CCD. The reflected beam is split by beamsplitter 50 into two sub-beams with intensities $I_x$ and $I_y$. Because of the way the beamsplitter works, the two sub-beams have different polarization states, as can be seen in FIG. 8 (by the circle and line in the reflected beams). An imposed retardation or phase shift $\delta$ between two polarization states in the incident beam becomes a phase difference $\Delta$ between complex amplitudes of the reflected and split sub-beams.

The elliptically polarized beam can be reconstructed at the camera by combining the two intensities, $I_x$ and $I_y$, which are the two measured intensities of beams with a relative phase-shift $\delta$ caused by the variable retarder 110 and which represent the intensities of the two differently polarized beams.

The average intensity of the polarization beams, m, is given with the following formula:

$$m = I_x + I_y \quad (3),$$

wherein difference d between the intensities is:

$$d = I_y - I_x \quad (4)$$

For surfaces without grating structures, the reflectance for p ($R_p$) and s ($R_s$) are essentially independent of the azimuth angle A, which holds for most blank surfaces that are used for calibration purposes. This means that reflectance coefficients of the two polarized sub-beams $R_p$ and $R_s$ (and combinations thereof) are not functions of A. Intensity I, on the other hand, is dependent on A, as well as on reflectance R.

The average intensity m is not dependant on retardation ($\delta$) because the two intensities of the polarized sub-beams are merely added together and a single resultant intensity can be easily measured at the detector:

$$m = I_x + I_y = Rp^2(C_4 + C_2 S_2) + Rs^2(S_4 + C_2 S_2)$$

so $$m = 0.5(Rp^2 + Rs^2) + 0.5C(2A)(Rp^2 - Rs^2) \quad (5)$$

wherein $$C_4 = \cos^4(A)$$

$$S_4 = \sin^4(A)$$

$$C_2 S_2 = \cos^2(A)\sin^2(A)$$

$$C_3 S = \cos^3(A)\sin(A)$$

$$C S_3 = \cos(A)\sin^3(A)$$

$$C(2A) = \cos(2A) \quad (6)$$

Knowing azimuth angle A of the incident beam and m from detector measurement, $\tan \Psi$ can be derived using the following into equation (5):

$$\tan \psi = \frac{Rp}{Rs} \text{ or } \psi = \arctan\left(\frac{Rp}{Rs}\right) \quad (7), (8)$$

On the other hand, when considering the difference between the intensities, as there is a phase difference between the two sub-beams with different polarization states, determining the difference between the intensities of the two states must take that phase difference into account. Furthermore, the difference in intensity between the two sub-beams is dependent both on the applied phase-shift or retardation $\delta$ and on the resultant phase difference after reflection $\Delta$.

Using the general expressions:

$$2 \times Iy = Rp \times (C_4 + C_2 S_2) + Rs^2(S_4 + C_2 S_2) + \{Rp^2(C_4 - C_2 S_2) + Rs^2(S_4 - C_2 S_2)\} \times \cos(\delta) + \ldots + RpRs \times \{\cos(\Delta) \times \cos(\delta) \times 4C_2 S_2 + \sin(\Delta) \times \sin(\delta) \times 2(C_3 S + C S_3)\}$$

and $$2 \times Ix = Rp \times (C_4 + C_2 S_2) + Rs^2(S_4 + C_2 S_2) - \{Rp^2(C_4 - C_2 S_2) + Rs^2(S_4 - C_2 S_2)\} \times \cos(\delta) + \ldots - RpRs \times \{\cos(\Delta) \times \cos(\delta) \times 4C_2 S_2 + \sin(\Delta) \times \sin(\delta) \times 2(C_3 S + C S_3)\}$$

the difference between the intensities may therefore given as:

$$d = I_y - I_x = \{Rp^2(C_4 - C_2 S_2) + Rs^2(S_4 - C_2 S_2)\} \cos(\delta) + \ldots RpRs\{\cos(\Delta)\cos(\delta)4C_2 S_2 + \sin(\Delta)\sin(\delta)2(C_3 S + C S_3)\} \quad (9)$$

Cos $\Delta$ (phase difference between the polarization states) is easily obtained when $\delta$ is known or indeed applied by the variable retarder 110.

For a number of chosen phase shifts $\delta$, functions m and d($\delta$) can be recorded. Every pupil data point of the function d($\delta$) is periodic. With a Fourier algorithm, the exact relative phase with respect to $\delta = 0$ can be obtained for every pupil data point. This file with relative phases is given as $\Delta_{Fourier}$. From this file, the unknown x can be solved for the complete pupil in the following equation:

$$\tan(\Delta_{Fourier}) = \frac{(2C_3 S + 2C S_3) \times \sqrt{1 - x^2}}{(C_4 - C_2 S_2) \times \tan(\psi) + \frac{(S_4 - C_2 S_2)}{\tan(\psi)} + 4C_2 S_2 x}$$

If $x = \cos(\Delta)$, the ellipsometric $\Delta$ is found for all azimuths.

Figure 10:
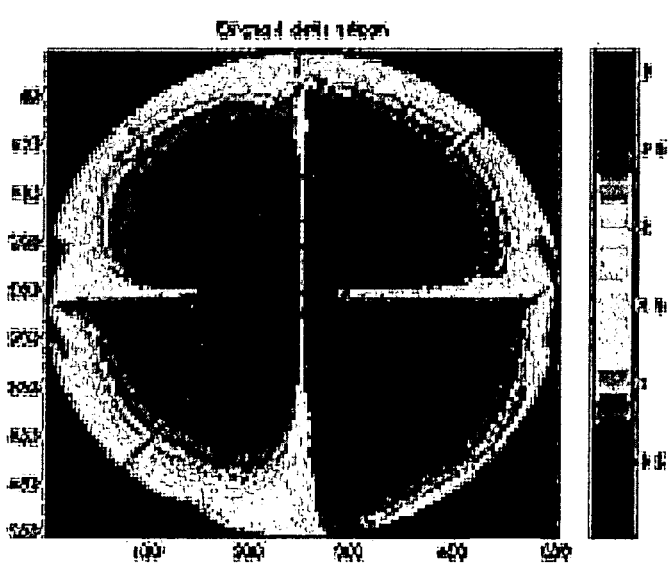

The examples shown in FIGS. 9 and 10 are the ellipsometric $\Psi$ and $\Delta$ measurements in polar pupil coordinates. The actual parameters were the use of silicon with radiation with a wavelength of 550 nm and a numerical aperture NA of 0 to 0.92.

Whether during calibration or reconstruction of a structure on the substrate W, the elliptically polarized beam is reconstructed for known values of $I_x$ and $I_y$. Applying the relationship of the intensity of the elliptically polarized beam to the amplitude of the individual components gives the amplitudes that can be input into equations (1) and (2) above. The reconstructed beam thereby gives the phase difference ($\Delta$) and relative amplitude alignment (i.e. ratio) (tan $\Psi$), thus giving rise to the parameters of the structure 30. In other words, the desired parameters, $\Delta$ and $\Psi$, can be determined by measuring the average of the two received intensities at each pixel and the difference between the two intensities for each pixel that is measured on the CCD camera of FIG. 6, as long as the retardation $\delta$ is known.

FIGS. 9 and 10 depict ellipsometric data as received by the camera CCD of FIG. 5. The numbers on the axes of FIGS. 9 and 10 are pixel numbers from the CCD camera and the image is the same as that at the pupil plane of the microscope objective that picks up the reflected and scattered radiation from the surface of the substrate. The centre point of each figure is the centre of the pupil plane, representing radiation traveling on the normal. The edge of the "lot" or substrate W is imaged at the edge of the pupil plane and the pixels on this part of the image show radiation that has reflected at a maximum angle, for example, 80° to the normal.

The evaluation of Ψ and Δ from the average intensity m and the difference in intensity d is shown in FIGS. 9 and 10 respectively. The evaluation is carried out using the equations (5) and (9) listed above.

FIG. 9 shows the pixel values for Ψ, derived using the knowledge of the value of m from its detection at the camera and its insertion into equation (5). The pixel values of Δ are shown in FIG. 10, with the values of d as determined from equation (9) and of δ as input by the variable retarder. FIGS. 9 and 10 depict a variation in both Ψ and Δ that can be measured and interpreted to derive the shape of the surface from which the radiation beam has been deflected. Asymmetry in the images as well as the variation in shade from the outside to the centre of the image give rise to measurable variation in parameters that can be used to reconstruct the radiation beam as it was received by the detector and thereby to determine the effect that the substrate surface had on the radiation beam. The effect of the surface on the radiation beam is directly linked to the shape of any object on the surface and so this can be derived.

The variation in Ψ and Δ can therefore be determined from the ellipsometric data as shown in FIGS. 9 and 10. The benefits of the described apparatus and method is that intensities may be measured simultaneously so that no measurement time is lost and the measurement is indeed as quick as a basic scatterometer, but with the benefit of having the separate measurements of the separate polarization states. This enables the use of a pulsed radiation source such as a laser. Furthermore, the phase-shifter allows for the measurement at every azimuthal angle. This means that less hardware needs to be added to an existing scatterometer in order to be able to allow much greater depth of analysis. Specifically, the described ellipsometer allows full-pupil analysis of measurements, not only on the azimuth angles A=45° and A=135° diagonals. This full-pupil approach has not previously been possible because all of the angles of reflectance have not previously been useable as they are in equations (5) and (9) above.

Experimentally, as a result of the above procedure to obtain data from a whole pupil, as opposed to just the diagonal, an increase of 200 times the number of available data points can be accomplished in the same exposure time. The above procedure can also be used for a portion of the pupil, if this is preferred. If, for example, a selection of 0.2 radians out of the pupil is used (out of a possible 2π), the above procedure enables the acquisition of 25 times more data points for Δ than ellipsometric data obtained only from diagonal points. This in turn gives rise to an increase in 5 times the signal-to-noise ratio.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. . . . The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam", as well as "light" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus comprising:
   an optical element configured to focus a radiation beam onto a substrate at a range of incident and azimuth angles such that the radiation beam reflects from the substrate;
   a polarizing device configured to polarize the reflected radiation beam into two different polarization directions;
   a variable retarder configured to retard at least one of the two different polarization directions by a certain amount so as to apply a variable phase shift on the reflected radiation beam, the variable phase shift being dependent on a wavelength of the radiation beam; and
   a detector system configured to detect simultaneously an angle-resolved spectrum of the two different polarization directions of the radiation beam.

2. The inspection apparatus according to claim 1, wherein, if the applied variable phase shift is δ, the detector system is configured to:
   output relative intensities of the two different polarization directions of the radiation beam,
   output a sum of the intensities of the two different polarization directions and a difference between the intensities of the two different polarization directions, apply an algorithm for each phase shift to output a file of relative phase differences ($\Delta_{Fourier}$), and $$\text{solve } \tan(\Delta_{Fourier}) = \frac{(2C_3S + 2CS_3) \times \sqrt{1-x^2}}{(C_4 - C_2S_2) \times \tan(\psi) + \frac{(S_4 - C_2S_2)}{\tan(\psi)} + 4C_2S_2x}$$

where $x=\cos(\Delta)$, $C_n=\cos^n(A)$, $S_n=\sin^n(A)$, $S=\sin(A)$ and $\Psi$=the angle between the two polarization directions, to obtain the value of relative phase differences ($\Delta$) between the two polarization directions for all azimuth angles (A).

3. The inspection apparatus according to claim 1, wherein the range of incident angles is about 0 to 80 degrees and the range of azimuth angles is about 0 to 360 degrees.

4. The inspection apparatus according to claim 1, wherein the variable phase shift is from about 0 to 360 degrees.

5. The inspection apparatus according to claim 1, further comprising a polarizing beamsplitter positioned downstream of the variable retarder and configured to split the phase-shifted radiation beam into two differently-polarized radiation sub-beams.

6. The inspection apparatus according to claim 1, wherein the polarizing device and variable retarder are configured to cause the radiation beam reflected from the substrate to be elliptically polarized.

7. The inspection apparatus according to claim 1, further comprising a focusing system and an optical wedge placed in an image plane of the focusing system configured to redirect the beam in different directions in dependence on the polarization directions, such that separate polarized reflected radiation sub-beams are received at different positions on the detector system.

8. The inspection apparatus according to claim 1, further comprising a processor configured to:
measure an azimuth angle of the radiation beam;
detect a summed intensity of polarized reflected radiation sub-beams;
derive a reflectance of the polarized reflected radiation sub-beams from the azimuth angle and presummed intensity;
evaluate a ratio between polarization direction amplitudes of the polarized reflected radiation sub-beams; and
determine a property of the substrate surface resulting from a variation from a predetermined model of the ratio between the polarization direction amplitudes of the polarized reflected radiation sub-beams.

9. The inspection apparatus according to claim 8, wherein the reflectance of the polarized reflected radiation sub-beams is derived using the equation:

$$m=0.5(Rp^2+Rs^2)+0.5\cos(2A)(Rp^2-Rs^2),$$

where the summed intensity (m) is known from the detector, wherein Rp and Rs are the reflectances from the polarized reflected radiation sub-beams and A is the azimuth angle of the radiation beam.

10. The inspection apparatus according to claim 8, wherein the ratio ($\tan \psi$) between the polarization direction amplitudes of the polarized reflected radiation sub-beams is evaluated using the equation:

$$\tan \Psi = Rp/Rs,$$

wherein Rp and Rs are the reflectances from the polarized reflected radiation sub-beams.

11. The inspection apparatus according to claim 1, wherein the polarizing device further comprises a retarder such that the radiation is circularly polarized.

12. The inspection apparatus according to claim 1, further comprising a processor configured to:
measure an azimuth angle of the radiation beam;
determine a value of the phase shift between polarized reflected radiation sub-beams prior to reflection from the substrate surface;
calculate a difference between the intensities of the polarized reflected radiation sub-beams from the azimuth angle and the phase shift;
derive a phase difference between the polarization directions of the polarized reflected radiation sub-beams post-reflection from the difference between the intensities of the sub-beams; and
determine a property of the substrate surface resulting from a variation from a predetermined model of the phase difference between the polarization directions of the polarized reflected radiation sub-beams.

13. The inspection apparatus according to claim 12, wherein the phase difference ($\Delta$) between the polarization direction of the polarized reflected radiation sub-beams post-reflection from a difference (d) between the intensities of the sub-beams is derived using the equation:

$$d=I_y-I_x=\{Rp^2(\cos^4(A)-\cos^2(A)\sin^2(A))+Rs^2(\sin(A)-\cos^2(A)\sin^2(A))\}\cos(\delta)+\ldots RpRs\{\cos(\Delta)\cos(\delta)4\cos^2(A)\sin^2(A)+\sin(\Delta)\sin(\delta)2(\cos^3(A)\sin(A)+\cos(A)\sin^3(A))\}$$

wherein Rp and Rs are the reflectances from the polarized reflected radiation sub-beams, A is the azimuth angle of the radiation Learn, $\delta$ is the phase shift, and Ix and Iy are the intensities of the sub-beams.

14. A method comprising:
providing a radiation beam with elliptical polarization;
reflecting the radiation beam off the surface of a substrate;
splitting the reflected radiation beam into two polarized sub-beams;
shifting a phase of a first sub-beam of the two sub-beams by a variable amount with respect to the second sub-beam of the two sub-beams, the variable amount being dependent on the wavelength of the radiation beam; and
simultaneously detecting the sub-beams.

15. The method according to claim 14, further comprising:
measuring an azimuth angle of the radiation beam;
detecting a summed intensity of the sub-beams;
deriving a reflectance of the sub-beams from the azimuth angle and the summed intensity;
evaluating a ratio between polarization direction amplitudes of the sub-beams; and
determining a property of the substrate surface resulting from a variation from a predetermined model of the ratio between the polarization direction amplitudes of the sub-beams.

16. The method, according to claim 15, wherein:
the reflectance of the sub-beams is derived by inserting the azimuth angle and the summed intensity into the equation:

$$m=0.5(Rp^2+Rs^2)+0.5\cos(2A)(Rp^2-Rs^2),$$

wherein Rp and Rs are the reflectances of the sub-beams, A is the azimuth angle of the radiation beam and m is the summed intensity of the sub-beams; and
wherein the ratio ($\tan \Psi$) between the polarization direction amplitudes of the sub-beams is evaluated using the equation:

$$\tan \Psi = Rp/Rs.$$

17. The method according to claim 14, further comprising:
measuring an azimuth angle of the radiation beam;
determining a value of the phase shift between the sub-beams prior to reflection from the substrate surface;
calculating a difference between intensities of the sub-beams;
deriving a phase difference between polarization directions of the sub-beams post-reflection; and
determining a property of the substrate surface resulting from a variation from a predetermined model of the phase difference between the polarization directions of the sub-beams.

18. The method according to claim 17, wherein:
a difference (d) between the intensities of the sub-beams is calculated using the equation:

$$d = I_y - I_x,$$

wherein Ix and Iy are the intensities of the sub-beams; and
wherein the phase difference ($\Delta$) between the polarization directions of the sub-beams post-reflection is derived using the equation:

$$d = I_y - I_x = \{Rp^2(\cos^4(A) - \cos^2(A)\sin^2(A)) + Rs^2(\sin(A) - \cos^2(A)\sin^2(A))\}\cos(\delta) + \ldots RpRs\{\cos(\Delta)\cos(\delta)4\cos^2(A)\sin^2(A) + \sin(\Delta)\sin(\delta)2(\cos^3(A)\sin(A) + \cos(A)\sin^3(A))\}$$

wherein Rp and Rs are the reflectances of the sub-beams, A is the azimuth angle of the radiation beam and S is the phase shift.

19. A lithographic apparatus comprising:
an optical element configured to focus a radiation beam onto a substrate at a range of incident and azimuth angles such that the radiation beam reflects from the substrate;
a polarizing device configured to polarize the reflected radiation beam into two different polarization orientations;
a variable retarder with a variable phase shift configured to shift a phase of the reflected radiation beam, the variable phase shift being dependent on the wavelength of the radiation beam; and
a detector system configured to detect simultaneously an angle-resolved spectrum of the two polarization orientations of the radiation beam.

20. A lithographic cell comprising:
a radiation source configured to supply a radiation beam;
an optical element configured to focus a radiation beam onto a substrate at a range of incident and azimuth angles such that the radiation beam reflects from the substrate;
a polarizing device configured to polarize the reflected radiation beam into two different polarization orientations;
a variable retarder with a variable phase shift configured to shift a phase of the reflected radiation beam, the variable phase shift being dependent on the wavelength of the radiation beam; and
a detector system configured to detect simultaneously an angle-resolved spectrum of the two polarization orientations of the radiation beam.

* * * * *

UNITED STATES PATENT AND TRADEMARK OFFICE
CERTIFICATE OF CORRECTION

PATENT NO. : 8,681,312 B2
APPLICATION NO. : 12/920968
DATED : March 25, 2014
INVENTOR(S) : Alexander Straaijer Page 1 of 1

It is certified that error appears in the above-identified patent and that said Letters Patent is hereby corrected as shown below:

In the Claims

In claim 13, column 18, lines 25-28, please delete equation
"$d=I_y-I_x=\{Rp^2(\cos^4(A)-\cos^2(A)\sin^2(A))+Rs^2(\sin(A)-\cos^2(A)\sin^2(A))\}\cos(\delta)+\ldots RpRs\{\cos(\Delta)\cos(\delta)4\cos^2(A)\sin^2(A)+\sin(\Delta)\sin(\delta)2(\cos^3(A)\sin(A)+\cos(A)\sin^3(A))\}$"
and insert $$d = I_y - I_x = \left\{Rp^2(\cos^4(A) - \cos^2(A)\sin^2(A)) + Rs^2(\sin^4(A) - \cos^2(A)\sin^2(A))\right\}\cos(\delta)+\ldots$$
$$\ldots RpRs\left\{\cos(\Delta)\cos(\delta)4\cos^2(A)\sin^2(A) + \sin(\Delta)\sin(\delta)2(\cos^3(A)\sin(A) + \cos(A)\sin^3(A))\right\}$$

-- --

In claim 13, column 18, line 30, please delete "Learn" and insert --beam--

In claim 18, column 19, lines 23-26, please delete equation

"$d=I_y-I_x=\{Rp^2(\cos^4(A)-\cos^2(A)\sin^2(A))+Rs^2(\sin(A)-\cos^2(A)\sin^2(A))\}\cos(\delta)+\ldots RpRs\{\cos(\Delta)\cos(\delta)4\cos^2(A)\sin^2(A)+\sin(\Delta)\sin(\delta)2(\cos^3(A)\sin(A)+\cos(A)\sin^3(A))\}$"
and insert $$d = I_y - I_x = \left\{Rp^2(\cos^4(A) - \cos^2(A)\sin^2(A)) + Rs^2(\sin^4(A) - \cos^2(A)\sin^2(A))\right\}\cos(\delta)+\ldots$$
$$\ldots RpRs\left\{\cos(\Delta)\cos(\delta)4\cos^2(A)\sin^2(A) + \sin(\Delta)\sin(\delta)2(\cos^3(A)\sin(A) + \cos(A)\sin^3(A))\right\}$$

-- --

Signed and Sealed this
Nineteenth Day of May, 2015

Michelle K. Lee
*Director of the United States Patent and Trademark Office*